(12) United States Patent
Bertrand et al.

(10) Patent No.: US 6,492,525 B1
(45) Date of Patent: Dec. 10, 2002

(54) ORGANOMETALLIC COMPLEXES COMPRISING CATIONIC HETEROCYCLIC CARBENES

(75) Inventors: Guy Bertrand, Pechbusque (FR); Lutz Stelzig, Münster (DE); Olivier Guerret, Marcy l'Etoile (FR); Christophe Buron, Toulouse (FR); Heinz Gornitzka, Toulouse (FR); Paolo Burattin, Lyons (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/700,768

(22) PCT Filed: May 11, 1999

(86) PCT No.: PCT/FR99/01128

§ 371 (c)(1),
(2), (4) Date: Jun. 21, 2001

(87) PCT Pub. No.: WO99/60004

PCT Pub. Date: Nov. 25, 1999

(30) Foreign Application Priority Data

May 20, 1998 (FR) .......................................... 98 06558

(51) Int. Cl.[7] .......................... C07F 19/00; C07F 7/14; B01J 31/00; C07C 45/80; C08F 4/04

(52) U.S. Cl. ................. 548/101; 548/262.2; 548/265.2; 548/265.8; 548/269.4; 502/155; 568/429; 568/451; 526/171; 526/172; 526/328; 585/250; 585/269; 585/478; 585/479

(58) Field of Search .............................. 548/101, 262.2, 548/265.8, 269.4; 502/155; 568/429, 451; 585/250, 269; 556/479, 478; 526/328, 171, 172

(56) References Cited

U.S. PATENT DOCUMENTS 4,339,448 A * 7/1982 Dockner et al. ............. 424/245

FOREIGN PATENT DOCUMENTS

| EP | 0 721 951 A | 12/1995 |
| EP | 0 721 953 A | 7/1996 |
| EP | 0 798 041 A | 10/1997 |
| WO | 97 34875 A | 9/1997 |

* cited by examiner

Primary Examiner—Porfirio Nazario-Gonzalez
(74) Attorney, Agent, or Firm—Burns, Doane, Swecker & Mathis, L.L.P.

(57) ABSTRACT

The invention concerns novel organometallic complexes comprising cationic heterocyclic carbenes. It also concerns a method for preparing said complexes from dicationic heterocyclic precursor compounds. It further concerns the use as catalysts of said organometallic complexes for a certain number of chemical reactions.

22 Claims, No Drawings

ORGANOMETALLIC COMPLEXES COMPRISING CATIONIC HETEROCYCLIC CARBENES

The present invention relates to novel organometallic complexes comprising cationic heterocyclic carbenes.

It also relates, as means for the preparation of such organometallic complexes, to dicationic heterocyclic precursor compounds.

A further subject-matter of the invention is a process for the preparation of the above organometallic complexes.

Finally, it also comprises the use, as catalysts, of the said organometallic complexes in a number of chemical reactions.

Organometallic complexes comprising heterocyclic carbenes have already been disclosed in the prior art. Thus, Patent EP-A-0,721,953 discloses complexes comprising noncationic heterocyclic carbenes derived from imidazoline or from pyrazoline and a metal from Groups 8, 9 and 10 of the Periodic Classification of the Elements. Patent EP-A-0,798,041 discloses complexes comprising noncationic heterocyclic carbenes derived from various compounds having 5-, 6- or 7-membered rings and comprising one or more nitrogen and/or sulphur atoms and a metal chosen from palladium, rhodium, nickel, ruthenium and cobalt.

Such complexes are very stable compounds which additionally have the advantage of not forming toxic byproducts during their decomposition. However, they exhibit the disadvantage of not being able to be used in an excessively acidic medium and complexes of metals with the 0 degree of oxidation are not soluble in water, which limits the field of their use.

The present invention therefore first of all relates to organometallic complexes comprising heterocyclic carbenes, characterized in that they correspond to the general formula (I)

$$[(Z^+X^-)_m ML_n]Y \quad (I)$$

in which:

Z$^+$ represents a 1,2,4-triazolium-5-ylidene ion, at least a portion of the atoms of the ring of which are substituted by hydrocarbon-comprising radicals, L represents a ligand, which can be ionic or neutral, M represents a metal chosen from the transition elements from Groups 1b, 2b, 3b, 4b, 5b, 6b, 7b and 8 of the Periodic Classification of the Elements as published in "Handbook of Chemistry and Physics, 51st Edition" (1970–1971) of The Chemical Rubber Company, X$^-$ represents an organic or inorganic anion, m represents an integer from 1 to 6, n represents an integer from 0 to 5, the sum of m and of n is equal to or less than 6, Y represents an anion or a cation such that the metal complex is electrically neutral.

For convenience, compounds of formula (I) also including the Y counterion are known as organometallic complexes or metal complexes in the present text.

The 1,2,4-triazolium-5-ylidene ions Z$^+$ correspond to the general formula (II):

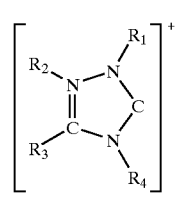

in which R$_1$, R$_2$, R$_3$ and R$_4$, which are identical or different, represent:

a linear or branched alkyl radical or a cycloalkyl radical, an aryl radical, an alkyl radical which comprises one or more substituents, such as an aryl radical, an alkoxy radical, a halogen atom or a hydrophilic group, for example:
—COOM$_1$, —SO$_3$M$_1$, or —PO$_3$M$_1$, M$_1$ representing an inorganic or organic cationic residue chosen from a proton, cations derived from alkali metals or alkaline earth metals, or ammonium cations —N(R)$_4$, in the formula of which cations the R symbols, which are identical or different, represent a hydrogen atom or an alkyl radical having from 1 to 4 carbon atoms,
—N(R)$_3$Y$_a$, in the formula of which the R symbols, which are identical or different, represent a hydrogen atom or an alkyl radical having from 1 to 12 carbon atoms and Y$_a$ represents an inorganic or organic anion,
—OH, an aryl or aralkyl or cycloalkyl radical which comprises, on the ring, one or more substituents, such as an alkyl radical, an alkoxy radical, a halogen atom or a hydrophilic group, for example:
—COOM$_1$, —SO$_3$M$_1$, or —PO$_3$M$_1$, M$_1$ representing an inorganic or organic cationic residue chosen from a proton, cations derived from alkali metals or alkaline earth metals, or ammonium cations —N(R)$_4$, in the formula of which cations the R symbols, which are identical or different, represent a hydrogen atom or an alkyl radical having from 1 to 12 carbon atoms,
—N(R)$_3$Y$_a$, in the formula of which the R symbols, which are identical or different, represent a hydrogen atom or an alkyl radical having from 1 to 12 carbon atoms and Y$_a$ represents an inorganic or organic anion,
—OH, R$_3$ also represents a hydrogen atom, R$_1$ and/or R$_4$ can also each represent an organic ligand residue bonded to the nitrogen atom of the 1,2,4-triazolium-5-ylidene ion via an alkylene or arylene radical, it being possible for the said ligand residue to be a phosphite residue, a phosphonite residue, a phosphinite residue, a phosphine residue or an amine residue which is tertiary and aliphatic, cycloaliphatic, aromatic or heterocyclic and which acts as ligand L to the metal M.

The preceding organic ligand residues can derive, for example, from phenyl or alkyl phosphites, substituted or unsubstituted by substituents as defined above, or from phenyl or alkyl phosphinites, substituted or unsubstituted by substituents as defined above, or from phenyl or alkyl phosphonites, substituted or unsubstituted by substituents as defined above, or from phenylphosphines or alkylphosphines, substituted or unsubstituted by substituents as defined above.

In such a case, the 1,2,4-triazolium-5-ylidene ion substituted by a R$_1$ and/or R$_4$ radical as defined above is a bidentate or tridentate ligand.

L represents an ionic ligand, such as a halide or a cyanide, or a neutral ligand, such as carbon monoxide, an isonitrile, a phosphine, an organic phosphite, a phosphonate or a phosphonite.

M preferably represents a metal chosen from nickel, cobalt, iron, ruthenium, rhodium, palladium, osmium, iridium, platinum, copper, silver, gold, zinc, cadmium or mercury.

These metals can be in their various degrees of oxidation, including the 0 degree of oxidation.

The $X^-$ anions are organic or inorganic anions, such as, for example, halides, but are preferably chosen from weakly coordinating anions which are defined with respect to the metal M under consideration. They predominantly constitute the counterions of the 1,2,4-triazolium-5-ylidene ions.

Mention may be made, as non-limiting examples of such weakly coordinating anions, of trifluoromethanesulphonate, tetrafluoroborate, hexafluorophosphate, aluminium tetrachloride, aluminium tetrabromide, aluminium tetrafluoride, aluminium tetraiodide, gallium tetrachloride, gallium tetrabromide, gallium tetrafluoride or gallium tetraiodide.

Another subject-matter of the present invention is the use of dicationic heterocyclic compounds as precursors in the preparation of the organometallic complexes of general formula (I). These dicationic heterocyclic compounds correspond to the general formula (III)

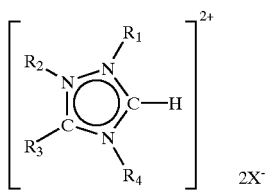

(III)

in which
the $R_1$, $R_2$, $R_3$ and $R_4$ symbols have the meanings shown above for the 1,2,4-triazolium-5-ylidene ions of formula (II),
—$X^{31}$ represents an anion such as those shown for the general formula (I).

The dicationic heterocyclic compounds of general formula (III) can be prepared by reacting a compound of formula $XR_2$, in which X and $R_2$ have the meanings shown above, with a triazole derivative carrying the $R_1$, $R_3$ and $R_4$ substituents. The preparation can also be carried out in several stages, each stage consisting in reacting a triazole derivative with a compound of formula $XR_1$ or $XR_3$ or $XR_4$, depending on the substituent which it is desired to introduce into the formula of the triazole employed, in order to obtain the dicationic heterocyclic compound of formula (III). The reaction conditions can be adapted from the procedure described in the article by T. J. Curphey and K. S. Prasad, Journal of Org. Chem., 1972, 37, 2259.

The organometallic complexes of formula (I) can be prepared by reacting a dicationic heterocyclic compound of general formula (III) with a compound of the metal M in the presence of an inorganic or organic base. Such a base can be the associated anion of the compound of the metal M or can be added independently to the reaction mixture. This reaction can be carried out in liquid medium, generally by adding the compound of the metal M and, if appropriate, the inorganic or organic base to the solution or suspension of the compound (III). Very clearly, the order of introduction of the various reactants can be modified. The reaction can be carried out at room temperature or, preferably, at a temperature of 25° C. to 150° C., for example. This temperature can conveniently be that of the reflux of the liquid in which the synthesis is carried out. The separation of the complex of formula (I) can be carried out according to the methods commonly used in chemistry, for example by filtration, by centrifuging or by extraction. The complexes of formula (I) and the dicationic heterocyclic compounds of formula (III) are generally characterized by Nuclear Magnetic Resonance (NMR) or by Infrared or by X-ray diffraction.

The organometallic complexes of formula (I) can be used as catalysts in numerous chemical reactions.

The majority of the organometallic complexes of formula (I) as well as the dicationic heterocyclic compounds of formula (III) have little solubility in or are insoluble in the majority of nonpolar or only slightly polar organic solvents, such as alkanes, cycloalkanes, haloalkanes, aromatic hydrocarbons, alkylaromatic hydrocarbons or ethers. On the other hand, they are soluble in polar solvents. Thus, the dicationic compounds are soluble in particular in tetrahydrofuran, dimethyl sulphoxide (DMSO), nitrites (for example, acetonitrile) or water. Thus, the organometallic complexes of the invention are soluble in particular in nitrites (for example, acetonitrile), DMSO or water. These properties make possible easier separation of these various compounds, in particular by liquid/liquid extraction. Furthermore, they make it possible to carry out catalysis in two-phase medium.

Mention may be made, as non-limiting examples of such reactions, of the hydrosilylation of alkenes or of alkynes, in particular in the presence of ruthenium complexes, the hydrosilylation of ketones in the presence of ruthenium or rhodium complexes, the Heck reaction in the presence of palladium complexes, the hydrogenation of olefins, aldehydes, acids, enamides and nitroaromatic compounds in the presence of ruthenium, rhodium, platinum or palladium complexes, the hydroformylation and the hydrocarbonylation of olefins in the presence of rhodium complexes, the hydrocyanation of olefins in the presence of nickel complexes, the synthesis of furan in the presence of ruthenium complexes, the metathesis of olefins in the presence of ruthenium complexes, or the polymerization of acrylates in the presence of nickel complexes.

EXAMPLES OF THE SYNTHESIS OF PRECURSORS OF FORMULA (III)

Example 1

Synthesis of the Compound (IIIa)

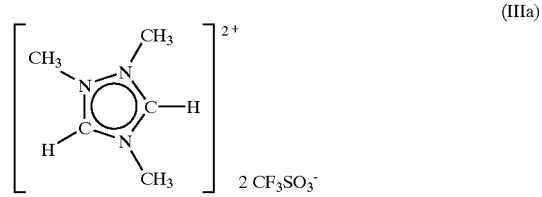

(IIIa)

By following the procedure described in J. Org. Chem., 1972, 37, page 2259, 1H-1,2,4-methyltriazole is methylated twice (at the 2 and 4 positions of the ring) with methyl trifluoromethanesulphonate at reflux in 1,2-dichloroethane with stirring.

The brown precipitate formed is filtered off and then washed with 1,2-dichloroethane until a white powder is obtained. This solid (IIIa) exhibits a melting point of 160–162° C.

It is characterized by:

$^1$H NMR (d$_6$-DMSO): δ 4.22 (s, 3H, CH$_3$N), 4.50 (s, 6H, CH$_3$N), 10.79 (s, 2H, H$_{cycle}$)

$^{13}$C NMR (H) (CD$_3$CN): δ 38.67 (s, CH$_3$N), 38.87 (s, 2CH$_3$N), 120.35 (q, $^1J_{CF}$=320.1 Hz, CF$_3$), 147.72 (s, 2C$_{cycle}$).

Example 2

Synthesis of the Compound (IIIb)

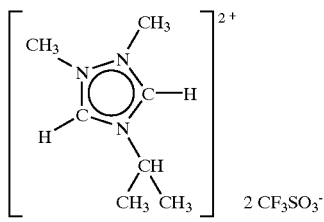

(IIIb)

The synthesis is carried out in two stages. First of all, an isopropyl group is attached at the 4 position (R$_4$ radical) by stoichiometric addition of 1H-1,2,4-methyltriazole to a solution of isopropyl trifluoromethanesulphonate in 1,2-dichloroethane (at reflux with stirring for 3 h). The compound of following formula:

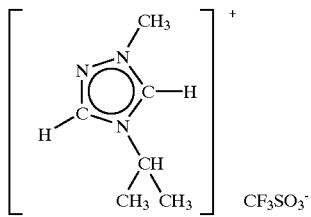

is obtained, with a yield of 91%, in the form of a yellow oil. 2.5 ml of methyl trifluoromethanesulphonate (22 mmol) are added to a solution of 5 g (18 mmol) of this compound in 20 ml of 1,2-dichloroethane and the mixture is brought to reflux with stirring for 24 h. A brown precipitate is formed, which precipitate is filtered off and then washed with 1,2-dichloroethane until a white powder is obtained. This solid (IIIb) exhibits a melting point of 163–165° C. and corresponds to a yield of 73% with respect to the intermediate compound charged.

It is characterized by:

$^1$H NMR (CD$_3$CN): δ 1.65 (d, $^3J_{HH}$=6.58 Hz, 6H, C̲H$_3$CH) 4.34 (s, 3H, CH$_3$N), 5.03 (sept, $^3J_{HH}$=6.58 Hz, 1H, [CH$_3$]$_2$CH̲N), 10.22 (s, 2H, H$_{cycle}$)

$^{13}$C NMR (CD$_3$CN): δ 21.51 (s, C̲H$_3$CH), 38.71 (s, CH$_3$N), 58.88 (s, [CH$_3$]$_2$C̲HN), 120.35 (q, $^1J_{CF}$=320.1 Hz, CF$_3$), 145.22 (s, 2C$_{cycle}$)

Example 3

Synthesis of the Compound (IIIc)

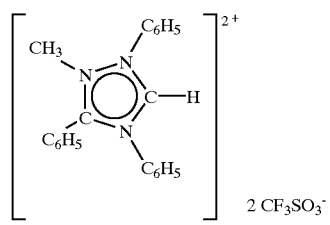

(IIIc)

The synthesis is carried out in two stages. First of all, the compound of following formula:

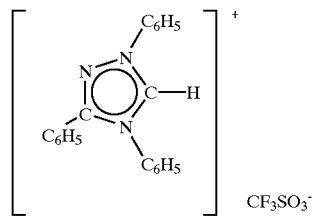

is prepared according to the procedure described in J. Prakt. Chem., 1988, 330, 3, 325.

This compound is heated at reflux in methyl trifluoromethanesulphonate with stirring for 4 days. A brown precipitate is formed, which precipitate is filtered off and then washed with 1,2-dichloroethane until a white powder is obtained. This solid (IIIc) is obtained with a yield of 50% with respect to the compound charged in the second stage.

It is characterized by:

$^1$H NMR (CD$_3$CN): δ 4.22 (s, 3H, CH$_3$N), 7.4–8.4 (unresolved peak, phenyl H), 10.34 (s, 1H, H$_{cycle}$)

Example 4

Synthesis of the Compound (IIId)

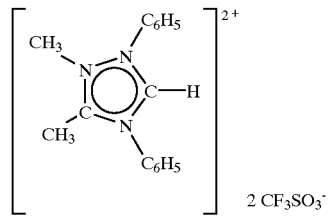

(IIId)

The synthesis is carried out in two stages. First of all, the compound of following formula:

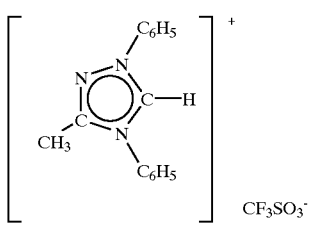

is prepared according to the procedure described in J. Prakt. Chem., 1988, 330, 31 325.

This compound is heated at reflux with 3 equivalents of methyl trifluoromethanesulphonate in 1,2-dichloroethane with stirring for 2 days. A brown precipitate is formed, which precipitate is filtered off and then washed with 1,2-dichloroethane until a white powder is obtained. This solid (IIId) is obtained with a yield of 69% with respect to the compound charged in the second stage and it exhibits a melting point of 190.5–191.3° C.

It is characterized by:

$^1$H NMR (CD$_3$CN): δ 3.04 (s, 3H, CH$_3$), 4.19 (s, 3H, CH$_3$N), 7.8–8.1 (unresolved peak, 10H, 1 phenyl H), 10.51 (s, 1H, H$_{cycle}$)

$^{13}$C NMR (CD$_3$CN): δ 12.31 (s, $\underline{C}$H$_3$C), 38.04 (s, CH$_3$N), 126.70 (s, 2 phenyl CH), 128.02 (s, phenyl C), 128.49 (s, 2 phenyl CH), 130.07 (s, phenyl C), 131.56 (s, 2 phenyl CH), 131.83 (s, 2 phenyl CH), 134.04 (s, 1 phenyl CH), 135.88 (s, 1 phenyl CH), 120.35 (q, $^1$J$_{CF}$=320. 1 Hz, CF$_3$), 145. 58 (s, CH$_{cycle}$), 157. 66 (s, C$_{cycle}$CH$_3$). The proton coupled spectrum shows a coupling constant $^1$J$_{CH}$=240 Hz for the CH of the triazole ring.

Example 5

Synthesis of the Compound (IIIe)

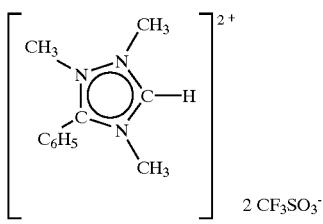

The synthesis is carried out in two stages. First of all, the compound of following formula:

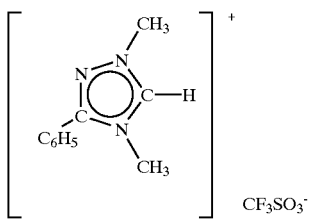

is prepared according to the procedure described in J. Prakt. Chem., 1988, 330, 3, 325.

This compound is heated at reflux with 3 equivalents of methyl trifluoromethanesulphonate in 1,2-dichloroethane with stirring for 2 days. A brown precipitate is formed, which precipitate is filtered off and then washed with 1,2-dichloroethane until a white powder is obtained. This solid (IIIe) is obtained with a yield of 71% with respect to the compound charged in the second stage and it exhibits a melting point of 180.0° C.

It is characterized by:

$^1$H NMR (CD$_3$CN): δ 4.08 (s, 3H, CH$_3$N), 4.20 (s, 3H, CH$_3$N), 4.46 (s, 3H, CH$_3$N), 7.8–8.1 (unresolved peak, 10H, 5 phenyl H), 10.16 (s, 1H, H$_{cycle}$).

$^{13}$C NMR (CD$_3$CN): δ 37.88 (s, $\underline{C}$H$_3$N), 38.36 (s, CH$_3$N), 39.42 (s, CH$_3$N), 130.78 (s, phenyl C), 131.97 (s, 2 phenyl CH), 132.15 (s, 2 phenyl CH), 137.35 (s, phenyl CH), 131.83 (s, 2 phenyl CH), 120.35 (q, $^1$J$_{CF}$=320.1 Hz, CF$_3$), 147.35 (s, CH$_{cycle}$), 156.48 (s, C$_{cycle}$).

Example 6

Synthesis of the Compound (IIIf)

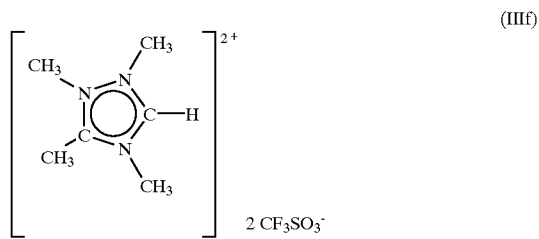

The synthesis is carried out in two stages. First of all, the compound of following formula:

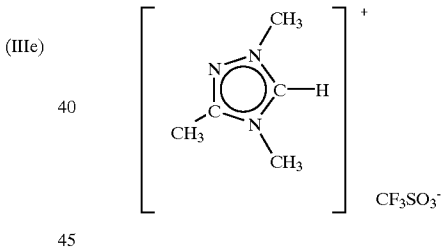

is prepared according to the procedure described in J. Prakt. Chem., 1988, 330, 3, 325.

This compound is heated at reflux with 3 equivalents of methyl trifluoromethanesulphonate in 1,2-dichloroethane with stirring for 2 days. A brown precipitate is formed, which precipitate is filtered off and then washed with 1,2-dichloroethane until a white powder is obtained. This solid (IIIf) is obtained with a yield of 95% with respect to the compound charged in the second stage and it exhibits a melting point of 194.4° C.

It is characterized by:

$^1$H NMR (d$_6$-acetone): δ 3.35 (s, 3H, CH$_3$C), 4.46 (s, 3H, CH$_3$N), 4.69 (s, 3H, CH$_3$N), 4.77 (s, 3H, CH$_3$N), 10.77 (s, 1H, H$_{cycle}$)

$^{13}$C NMR (d$_6$-acetone): δ 10.53 (s, $\underline{C}$H$_3$C), 35.91 (s, CH$_3$N), 36.26 (s, CH$_3$N), 37.99 (s, CH$_3$N), 120.35 (q, $^1$J$_{CF}$320. 1 Hz, CF$_3$), 145.35 (s, CH$_{cycle}$) 157.31 (s, $\underline{C}_{cycle}$CH$_3$)

EXAMPLES OF THE SYNTHESIS OF THE ORGANOMETALLIC COMPLEXES OF FORMULA (I)

Example 7

Synthesis of the Ag(I) Compound (Ia)

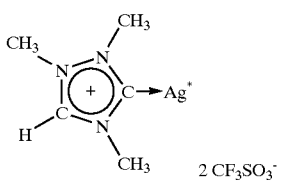
(Ia)

0.4 g (2.4 mmol) of Ag acetate is added to a suspension of 1 g of dicationic compound (IIIa), prepared in Example 1, in 20 ml of tetrahydrofuran (THF). The mixture is stirred for 2 h at reflux. A THF-immiscible brown oil is formed, which oil is washed several times with 10 ml of THF. After evaporating the solvent, a light-sensitive brown solid is obtained (a yield of 82% with respect to the dicationic compound (IIIa)).

This complex exhibits the following characteristics:

$^1$H NMR (CD$_3$CN): δ 4.01 (s, 3H, NCH$_3$), 4.19 (s, 3H, CH$_3$N—NCH$_3$), 4.22 (s, 3H, CH$_3$N—NCH$_3$), 9.72 (s, 1H, CH).

$^{13}$C NMR (CD$_3$CN): δ 37.2 (NCH$_3$), 38.5 (NCH$_3$), 38.6 (NCH$_3$), 121.1 (q, $^1J_{CF}$=320.1 Hz, CF$_3$), 144.8 (CH), 189.2 (CAg).

Example 8

Synthesis of the Hg(II) Compound (Ib)

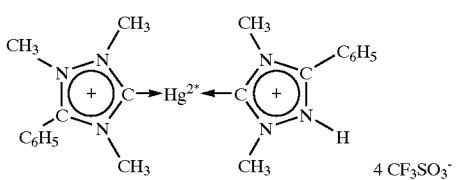

0.16 g of Hg diacetate (which was dried beforehand under vacuum for 12 h at 50° C.) and 1 ml of dimethyl sulphoxide (DMSO) are added to a suspension of 0.43 g of dicationic compound (IIIe), prepared in Example 5, in 20 ml of tetrahydrofuran (THF). The mixture is stirred for 24 h at ambient temperature. A brown precipitate is formed which is soluble solely in highly polar solvents. This solid is washed several times with THF in order to remove any traces of acetic acid. The complex thus obtained is recrystallized by slow diffusion of ether into a methanolic solution of the said complex. The recrystallized complex (Ib) exhibits a melting point of 85.4–87° C. A yield of 86% is obtained with respect to the dicationic compound (IIIe).

This complex exhibits the following characteristics:

$^1$H NMR (CD$_3$OD): δ 4.70 (s, 12H, NCH$_3$, $^4J_{H-Hg}$=12.8), 4.29 (s, 6H, CH$_3$N, $^4J_{H-Hg}$=8.5 Hz), 7.9–8.2 (unresolved peak, 10H, phenyl H).

$^{13}$C NMR (CD$_3$OD): δ 38.79 (CH$_3$N—NCH$_3$), 41.75 (NCH$_3$), 121.1 (q, $^1J_{CF}$=320.1 Hz, CF$_3$), 156.88 (C—Ph, ($^3$J+$^2$J)$_{C-Hg}$=86 Hz), 183.78 (CHg, $^1J_{CHg}$=3275 Hz)

This structure was also established by X-ray diffraction.

Example 9

Synthesis of the Ni(II) Compound (Ic)

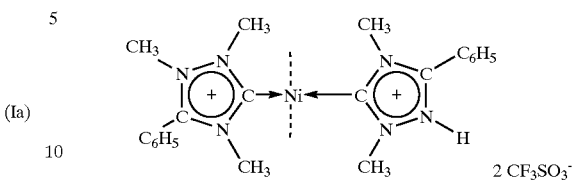

2.4g of dicationic compound (IIIe), prepared in Example 5, are added to a suspension of 0.442 g of Ni diacetate and 0.75 g of Na iodide in 50 ml of THF. The mixture is stirred at reflux for 2 h. A coloured precipitate is formed, which precipitate is filtered off and washed several times with THF. The complex thus obtained is recrystallized from an acetone/ether mixture at −30° C. The recrystallized complex (Ic) is red and it exhibits a melting point of 310.7° C. (decomposition: the crystals become black). A yield of 85% is obtained with respect to the dicationic compound (IIIe).

This complex exhibits the following characteristics:

$^1$H NMR (d$_6$-acetone): δ 7.8–8.0 (broad, 10H, phenyl H), 4.88–4.84 (2s, 6H, NCH$_3$), 4.54–4.49 (2s, 6H, CH$_3$N), 4.42–4.41 (2s, 6H, CH$_3$N).

$^{13}$C NMR (CD$_3$OD): δ 37.0 (CH$_3$N), 37.9 (CH$_3$N), 38.4 (CH$_3$N), 121.1 (q, $^1J_{CF}$=320. 1 Hz, CF$_3$), 130.5, 130.8 and 134.8 (phenyl C), 153.4 (C—Ph), 188.2 (C—Ni).

Its structure was also established by X-ray diffraction.

Example 10

Synthesis of the Ni(II) Compound (Id)

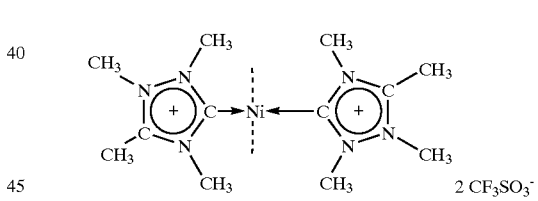

0.425 g of dicationic compound (IIIf), prepared in Example 6, is added to a suspension of 0.090 g of Ni diacetate and 0.15 g of Na iodide in 25 ml of THF. The mixture is stirred at reflux for 2 h. A coloured precipitate is formed, which precipitate is filtered off and washed several times with THF. The complex thus obtained is recrystallized from an acetone/ether mixture at −30° C. The recrystallized complex (Id) is red and it exhibits a melting point of 300–305° C. (decomposition: the crystals become black). A yield of 79% is obtained with respect to the dicationic compound (IIIf).

This complex exhibits the following characteristics:

$^1$H NMR (d$_6$-acetone): δ 4.88–4.84 (2s, 6H, NCH$_3$), 4.54–4.49 (2s, 6H, CH$_3$N), 4.42–4.41 (2s, 6H, CH$_3$N), 2.63 (s, 6H, C—CH$_3$).

$^{13}$C NMR (CD$_3$OD): δ 13.86 (C—CH$_3$), 36.1 (CH$_3$N), 37.6 (CH$_3$N), 38.5 (CH$_3$N), 121.1 (q, $^1J_{CF}$=320.1 Hz, CF$_3$), 154.8 (C—Me), 187.6 (C—Ni).

Its structure was also established by X-ray diffraction.

Example 11

Synthesis of the Ni(II) Compound (Ie)

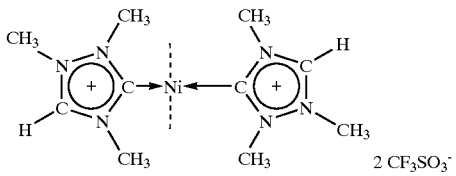

0.935 g of dicationic compound (IIIa), prepared in Example 1, is added to a suspension of 0.200 g of Ni diacetate and 0.34 g of Na iodide in 30 ml of THF. The mixture is stirred at reflux for 2 h. A coloured precipitate is formed, which precipitate is filtered off and washed several times with THF. The complex thus obtained is recrystallized by slow diffusion of ether into a solution of the said complex in acetonitrile. Recrystallization is carried out from an acetone/ether mixture at −30° C. The recrystallized complex (Ie) is red. A yield of 70% is obtained with respect to the dicationic compound (IIIa).

This complex exhibits the following characteristics:

$^1$H NMR (d$_6$-acetone): δ 4.38–4.35 (2s, 6H, CH$_3$N), 4.68–4.65 (2s, 6H, CH$_3$N), 4.99–4.96 (2s, 6H, NCH$_3$), 9.32 (s, 2H, C$\underline{H}$).

Example 12

Synthesis of the Pd(II) Compound (If)

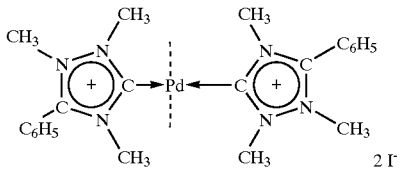

0.472 g of dicationic compound (IIIe), prepared in Example 5, is added to a suspension of 0.112 g of Pd diacetate and 0.30 g of Na iodide in 60 ml of THF. The mixture is stirred at reflux for 2 h. A coloured precipitate is formed, which precipitate is filtered off and washed several times with ether. The complex thus obtained is recrystallized at −30° C. from an acetone/ether mixture. It exists in the form of yellow crystals. The recrystallized complex (If) exhibits a melting point of 211–213° C. (decomposition: the crystals become brown). During the reaction, all the trifluoromethanesulphonate anions were substituted by iodide anions. A yield of 51% is obtained with respect to the dicationic compound (IIIe).

This complex exhibits the following characteristics:

$^1$H NMR (d$_6$-DMSO): δ 7.8–8.1 (broad, 10H, phenyl H), 4.49–4.53 (2s, 6H, NCH$_3$), 4.21 (s, 6H, CH$_3$N), 4.10–4.13 (2s, 6H, CH$_3$N).

$^{13}$C NMR (d$_6$-DMSO): δ 37.2 (CH$_3$N), 38.3 (CH$_3$N), 39.9 (CH$_3$N), 130.1, 130.9 and 134.5 (phenyl C), 152.4 ($\underline{C}$—Ph), 174.5 (C—Pd).

Its structure was also established by X-ray diffraction.

Example 13

Synthesis of the Pd(II) Compound (Ig)

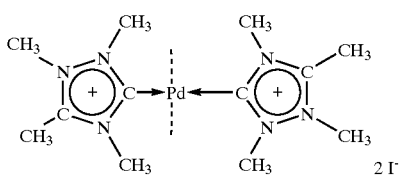

0.425 g of dicationic compound (IIIf), prepared in Example 6, is added to a suspension of 0.112 g of Pd diacetate and 0.30 g of Na iodide in 60 ml of THF. The mixture is stirred at reflux for 2 h. A coloured precipitate is formed, which precipitate is filtered off and washed several times with ether. The complex thus obtained is recrystallized at −30° C. from an acetone/ether mixture. It exists in the form of red crystals. The recrystallized complex (Ig) exhibits a melting point of 206–212° C. (decomposition: the crystals become brown). During the reaction, all the trifluoromethanesulphonate anions were substituted by iodide anions. A yield of 60% is obtained with respect to the dicationic compound (IIIf).

This complex exhibits the following characteristics:

$^1$H NMR (d$_6$-DMSO): δ 4.41–4.40 (2s, 6H, NCH$_3$), 4.29 (s, 6H, CH$_3$N), 4.16–4.15 (2s, 6H, CH$_3$N), 2.95 (6H, C—CH$_3$).

Example 14

Synthesis of the Ni(0) Compound (Ih)

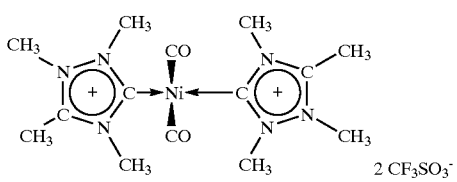

Synthetic Method A 1 ml of nickel tetracarbonyl is diluted in 40 ml of anhydrous and degassed acetonitrile. 380 μl of pyridine and 660 μl of triethylamine are added to the solution obtained.

A solution of 2.0 g of dicationic compound (IIIf), prepared in Example 6, in 60 ml of anhydrous and degassed acetonitrile is added dropwise using a dropping funnel. Gas is observed to be given off and the solution turns yellow in colour. When all the solution has been introduced, stirring is maintained for a further 1 h. The volume of the reaction solution is subsequently reduced by two thirds by evaporation of the solvent under vacuum and then 200 ml of degassed ether are added. A precipitate of the complex (Ih) is then formed, which precipitate is filtered off and washed several times with ether. The complex thus obtained is recrystallized from an acetone/ether mixture at −30° C. The complex (Ih) exists in the form of yellow crystals. Its melting point could not be determined exactly (decomposition: the crystals become brown). A yield of 26% is obtained with respect to the dicationic compound (IIIf).

This complex exhibits the following characteristics:

$^1$H NMR (d$_6$-DMSO): δ 4.00 (s, 6H, NCH$_3$), 3.99 (s, 6H, CH$_3$N), 3.78 (s, 6H, CH$_3$N), 2.72 (6H, C—C$\underline{H}_3$)

Bands at 1982 cm$^{-1}$ and 1906 cm$^{-1}$ (CO) are observed by Infrared spectrometry.

Its structure was also established by X-ray diffraction.

The following were found by elemental analysis:

28.99% of C (theory 28.89%)
3.36% of H (theory 3.63%)
12.39% of N (theory 12.62%).

Synthetic Method B 150 mg of activated metallic Zn powder (10 equivalents) are added to a solution of 0.2 g of the organometallic complex (Id), prepared in Example 10, in 10 ml of anhydrous and degassed acetonitrile. The solution is placed under a carbon monoxide atmosphere. The reaction begins at the same time as the stirring is begun. The solution becomes yellow. The solution is filtered using a tube and then it is treated in the way described for Method A (from the addition of ether in order to precipitate the organometallic complex). The yield obtained is 48% with respect to the organometallic complex (Id) charged. The same analyses and characterizations are carried out as in Method A and the results are the same.

Example 15

Synthesis of the Rh(I) Compound (Ij)

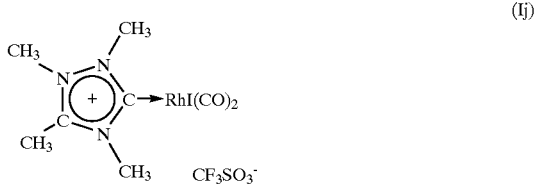

(Ij)

A solution of 0.277 g of di(carbonyl)rhodium acetylacetonate in 10 ml of THF is added to a suspension of 0.456 g of dicationic compound (IIIf), prepared in Example 6, and of 0.16 g of NaI in 40 ml of THF. The mixture is stirred at 50° C. for 2 days. A brown solid is recovered after evaporation of the solvent and washing several times with ether. The yield is 70% with respect to the dicationic compound (IIIf).

This complex exhibits the following characteristics:

$^1$H NMR (d$_6$-DMSO): δ 4.47 (s, 3H, NCH$_3$), 4.28 (s, 3H, CH$_3$N), 4.20 (s, 3H, CH$_3$N), 2.96 (s, 3H, C—CH$_3$).

$^{13}$C NMR (d$_6$-DMSO): δ 10.5 (s, C—$\underline{C}$H$_3$), 35.2 (s, NCH$_3$), 36.8 (s, CH$_3$N), 37.9 (s, CH$_3$N), 154.2 (s, $\underline{C}$—CH$_3$), 183.0 (d, $^1$J(Rh—C)=82.9 Hz, CO), 188.1 (d, $^1$J(Rh—C)=42.2 Hz, carbene C).

A band at 1975 cm$^{-1}$ (CO) is observed by Infrared.

Example 16

Synthesis of the Rh(I) Compound (Ik)

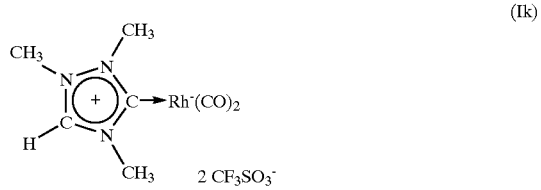

(Ik)

A solution of 0.200 g of di(carbonyl)rhodium acetylacetonate in 10 ml of THF is added to a suspension of 0.16 g of dicationic compound (IIIa), prepared in Example 1, in 10 ml of THF. The mixture is stirred at 50° C. for 15 h. A brown solid precipitate is formed, which precipitate is washed several times with ether. The yield of complex (Ik) is 67% with respect to the dicationic compound (IIIa).

This complex exhibits the following characteristics:

$^1$H NMR (d$_6$-DMSO): δ 4.20 (s, 3H, NCH$_3$), 4.22 (s, 3H, CH$_3$N), 4.25 (s, 3H, CH$_3$N), 9.66 (s, 1H, CH).

$^{13}$C NMR (d$_6$-DMSO): δ 38.6 (s, NCH$_3$), 38.7 (s, NCH$_3$) 39.1 (s, CH$_3$N), 37.9 (s, CH$_3$N), 121.1 (q, $^1$J$_{CF}$=320.1 Hz, CF$_3$), 145.5 (s, $\underline{C}$H), 186.1 (d, $^1$J(Rh—C)=76 Hz, CO), 187.9 (d, $^1$J(Rh—C)=43.3 Hz, carbene C).

Bands at 2029 (i) cm$^{-1}$ and 1985 (m) cm$^{-1}$ (CO) are observed by Infrared.

Example 17

Catalysis of the Hydroformylation of Styrene by the Rh(I) Compound (Ij)

The hydroformylation reaction of styrene is carried out in a 100 ml stainless steel reactor comprising a jacket allowing heating by circulation of oil at a temperature controlled using a thermostat. The lid of the reactor is equipped with a valve for introducing or discharging gases under pressure, with an accurate manometer, with a safety valve and with a ball valve allowing the transfer of solutions with a syringe. A Teflon® pot is fitted inside the autoclave and comprises a magnetic bar for stirring the reactants.

The Rh(I) complex (Ij) prepared in Example 15 is charged (40 mg) to the Teflon® pot, as well as 100 mg of triphenylphosphine (5 equivalents with respect to the catalyst). The autoclave is assembled and purged three times with argon. 15 ml of tetrahydrofuran, 5 ml of styrene and 60 mg of triethylamine (4 equivalents with respect to the catalyst) are subsequently charged. A carbon monoxide pressure (15 bar) and a hydrogen pressure (15 bar) are then established. The autoclave is heated to 60° C. with magnetic stirring. After reacting for 4 h at this temperature, the autoclave is quickly cooled in an acetone/liquid nitrogen mixture and depressurization is carried out over one hour. A sample of the reaction mixture is analysed by vapour phase chromatography (VPC).

The following results are obtained:
degree of conversion of the styrene: 95%
selectivity for aldehydes: 97%
branched aldehyde/linear aldehyde ratio: 95/5
frequency of rotation of the catalyst: 75 h$^{-1}$ (calculated by average with regard to the reaction time, taking an identical VPC response factor for all the products).

Example 18

Catalysis of the Hydroformylation of Styrene by the Rh(I) Compound (Ik)

Example 17 is repeated with 40 mg of complex (Ik) prepared in Example 16 and without employing triphenylphosphine.

After reacting for 3 h at 80° C., the autoclave is quickly cooled in an acetone/liquid nitrogen mixture and depressurization is carried out over one hour. A sample of the reaction mixture is analysed by vapour phase chromatography (VPC).

The following results are obtained:

degree of conversion of the styrene: 96% selectivity for aldehydes: 100% branched aldehyde/linear aldehyde ratio: 25/75 frequency of rotation of the catalyst: 79 h$^{-1}$ (calculated by average with regard to the reaction time, taking an identical VPC response factor for all the products).

What is claimed is:

1. An organometallic complex comprising a heterocyclic carbene corresponding to the general formula (I)

$$[(Z^+X^-)_m ML_n]Y \qquad (I)$$

in which:

- $Z^+$ represents a 1,2,4-triazolium-5-ylidene ion, at least a portion of the atoms of the ring of which are substituted by hydrocarbon-comprising radicals,
- L represents a ligand, which can be ionic or neutral,
- M represents a metal selected from the transition elements from Groups 1b, 2b, 3b, 4b, 5b, 6b, 7b and 8 of the Periodic Classification of the Elements,
- $X^-$ represents an organic or inorganic anion,
- m represents an integer from 1 to 6,
- n represents an integer from 0 to 5,
- the sum of m and of n is equal to or less than 6, and
- Y represents an anion or a cation such that the metal complex is electrically neutral.

2. The organometallic complex according to claim 1, wherein the 1,2,4-triazolium-5-ylidene ion $Z^+$ corresponds to the general formula (II):

$$\left[\begin{array}{c} R_1 \\ R_2-N\diagup N \\ \parallel \quad \diagdown C: \\ R_3-C-N \\ \qquad R_4 \end{array}\right]^+ \qquad (II)$$

in which $R_1$, $R_2$, $R_3$ and $R_4$, which are identical or different, represent:

- a linear or branched alkyl radical or a cycloalkyl radical,
- an aryl radical,
- an alkyl radical which comprises one or more substituents, comprising an aryl radical, an alkoxy radical, a halogen atom or a hydrophilic group comprising:
  - $—COOM_1$, $—SO_3M_1$, or $—PO_3M_1$, $M_1$ representing an inorganic or organic cationic residue selected from a proton, cations derived from alkali metals or alkaline earth metals, or ammonium cations $—N(R)_4$, in the formula of which cations the R symbols, which are identical or different, represent a hydrogen atom or an alkyl radical having from 1 to 4 carbon atoms,
  - $—N(R)_3Y_a$, in the formula of which the R symbols, which are identical or different, represent a hydrogen atom or an alkyl radical having from 1 to 12 carbon atoms and $Y_a$ represents an inorganic or organic anion, or
  - $—OH$,

- or an aryl or aralkyl or cycloalkyl radical which comprises, on the ring, one or more substituents, comprising an alkyl radical, an alkoxy radical, a halogen atom or a hydrophilic group, comprising:
  - $—COOM_1$, $—SO_3M_1$, or $—PO_3M_1$, $M_1$ representing an inorganic or organic cationic residue chosen from a proton, cations derived from alkali metals or alkaline earth metals, or ammonium cations $—N(R)_4$, in the formula of which cations the R symbols, which are identical or different, represent a hydrogen atom or an alkyl radical having from 1 to 12 carbon atoms,
  - $—N(R)_3Y_a$, in the formula of which the R symbols, which are identical or different, represent a hydrogen atom or an alkyl radical having from 1 to 12 carbon atoms and $Y_a$ represents an inorganic or organic anion, or
  - $—OH$, $R_3$ also represents a hydrogen atom, $R_1$ and/or $R_4$ can also each represent an organic ligand residue bonded to the nitrogen atom of the 1,2,4-triazolium-5-ylidene ion via an alkylene or arylene radical, it being possible for said ligand residue to be a phosphite residue, a phosphonite residue, a phosphinite residue, a phosphine residue or an amine residue which is tertiary and aliphatic, cycloaliphatic, aromatic or heterocyclic and which acts as ligand L to the metal M.

3. The organometallic complex according to claim 1, wherein $R_1$ and $R_4$ represent an organic ligand residue bonded to the nitrogen atom of the 1,2,4-triazolium-5-ylidene ion via an alkylene or phenylene radical, the said ligand residue deriving from phenyl or alkyl phosphites, substituted or unsubstituted, or from phenyl or alkyl phosphonites, substituted or unsubstituted, or from phenyl or alkyl phosphinites, substituted or unsubstituted, or from phenylphosphines or alkylphosphines, substituted or unsubstituted.

4. The organometallic complex according to claim 1, wherein L represents an ionic ligand selected from halides or cyanides or a neutral ligand selected from carbon monoxide, an isonitrile, a phosphine, an organic phosphite, a phosphonate or a phosphonite.

5. The organometallic complex according to claim 1, wherein M represents a metal selected from nickel, cobalt, iron, ruthenium, rhodium, palladium, osmium, iridium, platinum, copper, silver, gold, zinc, cadmium or mercury.

6. The organometallic complex according to claim 1, wherein the $X^-$ anion is a weakly coordinating anion and predominantly constitutes the counterion of the 1,2,4-triazolium-5-ylidene ion.

7. The organometallic complex according to claim 6, wherein the weakly coordinating anion $X^-$ is selected from trifluoromethanesulphonate, tetrafluoroborate, hexafluorophosphate, aluminum tetrachloride, aluminum tetrabromide, aluminum tetrafluoride, aluminum tetraiodide, gallium tetrachloride, gallium tetrabromide, gallium tetrafluoride or gallium tetraiodide.

8. Process for preparation of the organometallic complex of general formula (I) according to claim 1, wherein a dicationic heterocyclic compound of general formula (III):

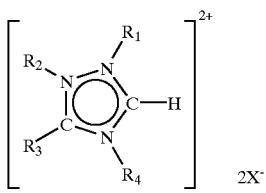

in which:
R₁, R₂, R₃ and R₄, which are identical or different, represent:
a linear or branched alkyl radical or a cycloalkyl radical,
an aryl radical,
an alkyl radical which comprises one or more substituents comprising an aryl radical, an alkoxy radical, a halogen atom or a hydrophilic group, comprising:
—COOM₁, —SO₃M₁, or —PO₃M₁, M₁ representing an inorganic or organic cationic residue selected from a proton, cations derived from alkali metals or alkaline earth metals, or ammonium cations —N(R)₄, in the formula of which cations the R symbols, which are identical or different, represent a hydrogen atom or an alkyl radical having from 1 to 4 carbon atoms,
—N(R)₃Y_a, in the formula of which the R symbols, which are identical or different, represent a hydrogen atom or an alkyl radical having from 1 to 12 carbon atoms and Y_a represents an inorganic or organic anion, or
—OH,
or an aryl or aralkyl or cycloalkyl radical which comprises, on the ring, one or more substituents, comprising an alkyl radical, an alkoxy radical, a halogen atom or a hydrophilic group, comprising:
—COOM₁, —SO₃M₁, or —PO₃M₁, M₁ representing an inorganic or organic cationic residue selected from a proton, cations derived from alkali metals or alkaline earth metals, or ammonium cations —N(R)₄, in the formula of which cations the R symbols, which are identical or different, represent a hydrogen atom or an alkyl radical having from 1 to 12 carbon atoms,
—N(R)₃Y_a, in the formula of which the R symbols, which are identical or different, represent a hydrogen atom or an alkyl radical having from 1 to 12 carbon atoms and Y_a represents an inorganic or organic anion, or
—OH,
R₃ also represents a hydrogen atom,
R₁ and/or R₄ can also each represent an organic ligand residue bonded to the nitrogen atom of the 1,2,4-triazolium-5-ylidene ion via an alkylene or arylene radical, it being possible for said ligand residue to be a phosphate residue, a phosphonite residue, a phosphinite residue, a phosphine residue or an amine residue which is tertiary and aliphatic, cycloaliphatic, aromatic or heterocyclic, and
X⁻ represents an organic or inorganic anion; is reacted with a compound of the metal M in the presence of an inorganic or organic base.

9. Preparation process according to claim 8, wherein the reaction is in liquid medium, the compound of the metal M and, optionally, the inorganic or organic base being added to the solution or suspension of the compound (III) or the preparation being carried out with another order of introduction of the reactants, at room temperature or, at a temperature of 25° C. to 150° C.

10. A catalyst for chemical reactions comprising the organometallic complex of formula (I) according to claim 1 on a support.

11. A method for the hydroformylation of olefins in the presence of rhodium complexes, comprising
contacting one or more olefins with an organometallic complex according to claim 1, wherein the metal of the organometallic complex comprises rhodium, and the amount of the organometallic complex is effective to provide a hydroformylation reaction product of the olefin(s).

12. A dicationic heterocyclic compound corresponding to the following general formula (III):

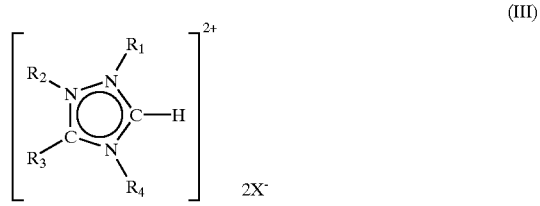

in which R₁, R₂, R₃ and R₄, which are identical or different, represent:
a linear or branched alkyl radical or a cycloalkyl radical,
an aryl radical,
an alkyl radical which comprises one or more substituents comprising an aryl radical, an alkoxy radical, a halogen atom or a hydrophilic group, comprising:
—COOM₁, —SO₃M₁, or —PO₃M₁, M₁ representing an inorganic or organic cationic residue selected from a proton, cations derived from alkali metals or alkaline earth metals, or ammonium cations —N(R)₄, in the formula of which cations the R symbols, which are identical or different, represent a hydrogen atom or an alkyl radical having from 1 to 4 carbon atoms,
—N(R)₃Y_a, in the formula of which the R symbols, which are identical or different, represent a hydrogen atom or an alkyl radical having from 1 to 12 carbon atoms and Y_a represents an inorganic or organic anion, or
—OH,
or an aryl or aralkyl or cycloalkyl radical which comprises, on the ring, one or more substituents, comprising an alkyl radical, an alkoxy radical, a halogen atom or a hydrophilic group, comprising:
—COOM₁, —SO₃M₁, or —PO₃M₁, M₁, representing an inorganic or organic cationic residue selected from a proton, cations derived from alkali metals or alkaline earth metals, or ammonium cations —N(R)₄, in the formula of which cations the R symbols, which are identical or different, represent a hydrogen atom or an alkyl radical having from 1 to 12 carbon atoms,
—N(R)₃Y_a, in the formula of which the R symbols, which are identical or different, represent a hydrogen atom or an alkyl radical having from 1 to 12 carbon atoms and $Y_a$ represents an inorganic or organic anion, or

—OH, $R_3$ also represents a hydrogen atom, $R_1$ and/or $R_4$ can also each represent an organic ligand residue bonded to the nitrogen atom of the 1,2,4-triazolium-5-ylidene ion via an alkylene or arylene radical, it being possible for the said ligand residue to be a phosphate residue, a phosphonite residue, a phosphinite residue, a phosphine residue or an amine residue which is tertiary and aliphatic, cycloaliphatic, aromatic or heterocyclic, and $X^-$ represents an organic or inorganic anion.

13. A compound according to claim 12, wherein the $X^-$ anion is a weakly coordinating anion and predominantly constitutes the counterion of the 1,2,4-triazolium-5-ylidene ion.

14. A compound according to claim 13, wherein the weakly coordinating anion $X^-$ is selected from trifluoromethanesulphonate, tetrafluorobroate, hexafluorophosphate, aluminum tetrachloride, aluminum tetrabromide, aluminum tetrafluoride, aluminum tetraiodide, gallium tetrachloride, gallium tetrabromide, gallium tetrafluoride or gallium tetraiodide.

15. Process for the manufacture of a dicationic heterocyclic compound according to claim 12, comprising reacting a compound of formula $XR_2$, with a monocationic triazoline derivative of the general formula:

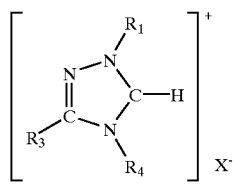

in which:

$R_1$, $R_2$, $R_3$ and $R_4$, which are identical or different, represent:

a linear or branched alkyl radical or a cycloalkyl radical, an aryl radical, an alkyl radical which comprises one or more substituents comprising an aryl radical, an alkoxy radical, a halogen atom or a hydrophilic group, comprising:

—$COOM_1$, —$SO_3M_1$, or —$PO_3M_1$, $M_1$ representing an inorganic or organic cationic residue selected from a proton, cations derived from alkali metals or alkaline earth metals, or ammonium cations —$N(R)_4$, in the formula of which cations the R symbols, which are identical or different, represent a hydrogen atom or an alkyl radical having from 1 to 4 carbon atoms, —$N(R)_3Y_a$, in the formula of which the R symbols, which are identical or different, represent a hydrogen atom or an alkyl radical having from 1 to 12 carbon atoms and $Y_a$ represents an inorganic or organic anion, or

—OH, or an aryl or aralkyl or cycloalkyl radical which comprises, on the ring, one or more substituents, comprising an alkyl radical, an alkoxy radical, a halogen atom or a hydrophilic group, comprising:

—$COOM_1$, —$SO_3M_1$, or —$PO_3M_1$, $M_1$ representing an inorganic or organic cationic residue selected from a proton, cations derived from alkali metals or alkaline earth metals, or ammonium cations —$N(R)_4$, in the formula of which cations the R symbols, which are identical or different, represent a hydrogen atom or an alkyl radical having from 1 to 12 carbon atoms, —$N(R)_3Y_a$, in the formula of which the R symbols, which are identical or different, represent a hydrogen atom or an alkyl radical having from 1 to 12 carbon atoms and $Y_a$ represents an inorganic or organic anion, or

—OH, $R_3$ also represents a hydrogen atom, $R_1$ and/or $R_4$ can also each represent an organic ligand residue bonded to the nitrogen atom of the 1,2,4-triazolium-5-ylidene ion via an alkylene or arylene radical, it being possible for said ligand residue to be a phosphate residue, a phosphonite residue, a phosphinite residue, a phosphine residue or an amine residue which is tertiary and aliphatic, cycloaliphatic, aromatic or heterocyclic, and $X^-$ represents an organic or inorganic anion.

16. A method for the hydrosilylation of alkenes or of alkynes, in the presence of a ruthenium complex, comprising contacting one or more alkenes or alkynes with an organometallic complex according to claim 1, wherein the metal of the organometallic complex comprises ruthenium, and the amount of the organometallic complex is effective to provide a hydrosilylation reaction product of the alkene(s) or alkyne(s).

17. A method for the hydrosilylation of ketones in the presence of a ruthenium or rhodium complex, comprising contacting one or more ketones with an organometallic complex according to claim 1, wherein the metal of the organometallic complex comprises ruthenium or rhodium, and the amount of the organometallic complex is effective to provide a hydrosilylation reaction product of the ketone(s).

18. A method for the hydrogenation of olefins, aldehydes, acids, enamides and nitroaromatic compounds in the presence of a ruthenium, rhodium, platinum or palladium complex, comprising contacting one or more olefins, aldehydes, acids, enamides or nitroaromatic compounds with an organometallic complex according to claim 1, wherein the metal of the organometallic complex comprises ruthenium, rhodium, platinum or palladium, and the amount of the organometallic complex is effective to provide a hydrogenation reaction product of the olefins, aldehydes, acids, enamides or nitroaromatic compounds(s).

19. A method for the hydrocarbonylation of olefins in the presence of a rhodium complex, comprising contacting one or more olefins with an organometallic complex according to claim 1, wherein the metal of the organometallic complex comprises rhodium, and the amount of the organometallic complex is effective to provide a hydrocarbonylation reaction product of the olefin(s).

20. A method for the the hydrocyanation of olefins in the presence of a nickel complex, comprising contacting one or more olefins with an organometallic complex according to claim 1, wherein the metal of the organometallic complex comprises nickel, and the amount of the organometallic complex is effective to provide a hydrocyanation reaction product of the olefin(s).

21. A method for metathesis of olefins in the presence of a ruthenium complex, comprising contacting one or more olefins with an organometallic complex according to claim 1, wherein the metal of the organometallic complex comprises ruthenium, and the amount of the organometallic complex is effective to provide a metathesis reaction product of the olefin(s).

22. A method for the polymerization of acrylates in the presence of a nickel complex, comprising contacting one or more acrylates with an organometallic complex according to claim 1, wherein the metal of the organometallic complex comprises nickel, and the amount of the organometallic complex is effective to provide a polymerization reaction product of the acrylate(s).

* * * * *